United States Patent
Galloway et al.

(10) Patent No.: US 10,349,927 B2
(45) Date of Patent: Jul. 16, 2019

(54) SOFT RETRACTORS

(71) Applicants: President and Fellows of Harvard College, Cambridge, MA (US); Soft Robotics Inc., Bedford, MA (US)

(72) Inventors: Kevin C. Galloway, Somerville, MA (US); Joshua Aaron Lessing, Cambridge, MA (US)

(73) Assignees: President and Fellows of Harvard College, Cambridge, MA (US); Soft Robotics Inc., Bedford, MA (US)

( * ) Notice: Subject to any disclaimer, the term of this patent is extended or adjusted under 35 U.S.C. 154(b) by 0 days.

(21) Appl. No.: 15/873,420

(22) Filed: Jan. 17, 2018

(65) Prior Publication Data

US 2019/0000435 A1  Jan. 3, 2019

Related U.S. Application Data

(63) Continuation of application No. 14/742,487, filed on Jun. 17, 2015, now Pat. No. 9,907,545.
(Continued)

(51) Int. Cl.
*A61B 17/00* (2006.01)
*A61B 17/02* (2006.01)
(Continued)

(52) U.S. Cl.
CPC .............. *A61B 17/02* (2013.01); *A61B 5/0538* (2013.01); *A61B 5/6865* (2013.01);
(Continued)

(58) Field of Classification Search
CPC .......................... A61B 17/02; A61B 17/0293; A61B 17/3423; A61B 2017/00026;
(Continued)

(56) References Cited

U.S. PATENT DOCUMENTS 4,501,264 A   2/1985  Rockey
4,784,042 A   11/1988 Paynter
(Continued)

FOREIGN PATENT DOCUMENTS

CN   101873832 A   10/2010
JP   S64-5540 A    1/1989
(Continued)

OTHER PUBLICATIONS

Extended European Search Report issued by the European Patent Office for European Application No. 15840171.1 dated May 23, 2018 (11 pages).
(Continued)

*Primary Examiner* — Pedro Philogene
(74) *Attorney, Agent, or Firm* — Wilmer Cutler Pickering Hale and Dorr LLP

(57) ABSTRACT

A soft material retractor includes at least two soft actuators, each actuator having at least one pressurizable interior space, wherein the actuator has a first flexible resting state and a second stiffer pressurized state; and a flexible sheet spanning the actuators such that the actuators can be spaced apart from each other by a distance selected to displace a volume of material of a body cavity. The retractor can be uses for holding open wounds or incisions, with trochars, or to displace anatomical features such as organs within a body cavity.

13 Claims, 19 Drawing Sheets

Related U.S. Application Data

(60) Provisional application No. 62/013,816, filed on Jun. 18, 2014.

(51) Int. Cl.

| | | |
|---|---|---|
| *A61B 17/34* | (2006.01) | |
| *A61B 5/00* | (2006.01) | |
| *A61B 5/053* | (2006.01) | |
| *A61B 5/145* | (2006.01) | |
| *A61B 90/30* | (2016.01) | |
| *A61B 90/98* | (2016.01) | |

(52) U.S. Cl.
CPC ...... *A61B 17/0293* (2013.01); *A61B 5/14546* (2013.01); *A61B 17/3423* (2013.01); *A61B 90/98* (2016.02); *A61B 2017/00026* (2013.01); *A61B 2017/00477* (2013.01); *A61B 2017/00557* (2013.01); *A61B 2090/309* (2016.02); *A61B 2217/005* (2013.01); *A61B 2217/007* (2013.01)

(58) Field of Classification Search
CPC A61B 2017/00477; A61B 2017/00557; A61B 2217/005; A61B 2217/007; A61B 5/0538; A61B 5/6865; A61B 5/14546; A61B 90/98; A61B 2090/309; B25J 15/08; B29C 31/002; B29L 2023/00; B05D 1/18; B05D 1/36; B05D 3/0254
USPC ...... 600/31, 115, 201–207, 470, 348; 92/92, 92/48, 261; 156/60, 163; 60/327, 484
See application file for complete search history.

(56) References Cited

U.S. PATENT DOCUMENTS

| | | |
|---|---|---|
| 4,984,564 A | 1/1991 | Yuen |
| 5,366,478 A | 11/1994 | Brinkerhoff et al. |
| 5,913,818 A | 6/1999 | Co et al. |
| 6,033,426 A | 3/2000 | Kaji |
| 6,033,428 A | 3/2000 | Sardella |
| 6,814,700 B1 | 11/2004 | Mueller et al. |
| 9,022,928 B2 | 5/2015 | Smith |
| 9,464,642 B2 * | 10/2016 | Ilievski .................. B25J 9/1075 |
| 2002/0013601 A1 | 1/2002 | Nobles et al. |
| 2002/0183594 A1 | 12/2002 | Beane et al. |
| 2003/0014076 A1 | 1/2003 | Mollenauer et al. |
| 2005/0245960 A1 | 11/2005 | Grundeman |
| 2010/0069947 A1 | 3/2010 | Sholev et al. |
| 2010/0261974 A1 | 10/2010 | Shelton, IV et al. |
| 2010/0312066 A1 * | 12/2010 | Cropper ............. A61B 17/3423 600/207 |
| 2011/0207102 A1 | 8/2011 | Trotta et al. |
| 2012/0078058 A1 | 3/2012 | Richard et al. |
| 2012/0238825 A1 | 9/2012 | Smith |
| 2016/0114482 A1 * | 4/2016 | Lessing .................. A61B 34/30 606/130 |
| 2017/0129111 A1 * | 5/2017 | Kim ....................... A61B 34/30 |

FOREIGN PATENT DOCUMENTS

| | | |
|---|---|---|
| JP | 2007/530128 A | 11/2007 |
| JP | 2009-500143 A | 1/2009 |
| JP | 2010-240435 A | 10/2010 |
| WO | WO-2005/089655 A1 | 9/2005 |
| WO | WO-2007/008417 A2 | 1/2007 |
| WO | WO-2009/070517 A2 | 6/2009 |
| WO | WO-2012/148472 A2 | 11/2012 |

OTHER PUBLICATIONS

Ilievski et al., (2011) "Soft robotics for chemists", Angew Chem Int Ed Engl, vol. 50, pp. 1890-1895.
International Search Report and Written Opinion dated Apr. 22, 2016, in the International Application No. PCT/US15/36281, filed on Jun. 17, 2015, 18 pages.
Partial Supplementary European Search Report issued by the European Patent Office for European Application No. 15840171.1 dated Jan. 26, 2018 (13 pages).
Shepherd et al., "Multigait soft robot," Proc. Natl. Acad. Sci. USA, Dec. 20, 2011, vol. 108, No. 51, pp. 20400-20403.

* cited by examiner

SOFT RETRACTORS

RELATED APPLICATIONS

This application is a continuation of U.S. patent application Ser. No. 14/742,487 filed Jun. 17, 2015, which claims the benefit of priority to U.S. Provisional Application No. 62/013,816, filed Jun. 18, 2014, the entirety of all of which is incorporated by reference.

STATEMENT REGARDING FEDERALLY FUNDED RESEARCH

This invention was made with support from the United States government under Grant No. N66001-13-C-4036 awarded by DARPA. The United States government has certain rights to this invention.

BACKGROUND

Field of the Invention

The present disclosure generally relates to the field of surgical instruments. In particular, the present disclosure relates to medical retractors and their methods of manufacture and use.

Background

Medical devices, such as surgical instruments (e.g. retractors, distractors, graspers, clamps, etc.), are typically constructed from hard materials that are poorly matched to the mechanical properties of biological structures (e.g. tissues, organs, blood vessels, nerves, etc.). More specifically, these tools are prone to creating stress concentrations that can result in tissue damage.

Medical devices that match the soft tissue properties of organs are needed.

SUMMARY

Medical devices are described that are made from lower stiffness materials that can conform to soft tissue and distribute forces over a larger contact area reducing the risk of tissue damage. Several soft retractors including an incision retractor, a pelvic retractor, and a general retractor for displacing anatomical structures are described.

In one aspect, a soft material retractor includes at least two soft actuators, each actuator comprising at least one pressurizable interior space, wherein the actuator comprises a first flexible resting state and a second stiffer pressurized state; and a flexible sheet spanning the actuators such that the actuators can be spaced apart from each other by a distance selected to displace a volume of material of a body cavity.

In one or more embodiments, the actuator spacing varies along the length of the actuators.

In one or more embodiments, the soft actuator includes fluidic interconnects suitable for connection of a single fluid pressurizing source or the soft actuator includes fluidic interconnects suitable for connection of a different fluid pressurizing sources to each actuator.

In one or more embodiments, the soft actuators bend upon fluid pressurization, or the soft actuators elongate upon fluid pressurization.

In one or more embodiments, the retractor includes a plurality of flexible sheets spanning the actuators and secured at intervals along the length of the actuators, wherein upon elongation of the actuator, expansion occurs primarily between the flexible sheets.

In one or more embodiments, the soft actuators are sized for insertion into an incision, wound or trochar.

In one or more embodiments, the distance is selected to span the thickness of a wall thickness of a body cavity, or the distance is selected to displace an anatomical structure within a body cavity.

In one or more embodiments, the flexible sheet is a plastic sheet, or the flexible sheet is a molded elastomer.

In any of the preceding embodiments, protruding features are incorporated into the flexible sheet.

In one or more embodiments, the flexible sheet can be plastically deformed to change the orientation and/or spacing of the soft actuators.

In one or more embodiments, the flexible sheet includes a reversible connective interface to change the spacing and/or orientation of the soft actuators and the reversible connective interface is selected from the group of hook and loop, reversible adhesives, and a pull string or adjustable cording.

In one or more embodiments, the soft material retractor further includes a flexible sleeve secured to the flexible sheet, wherein the at least two actuators are housed within the flexible sleeve.

In one or more embodiments, the flexible sleeve is a plastic sheet, or the flexible sleeve is thermally sealed around the soft actuators.

In one or more embodiments, the flexible sleeve is elastomeric and, for example, the flexible sleeve and the flexible sheet is overmolded onto the soft actuators.

In one or more embodiments, protruding features are incorporated into the flexible sleeve.

In one or more embodiments, the ends of the soft material retractor are configured to be connected end to end to form a loop, and for example, the soft material retractor grows radially upon pressurization.

In any of the preceding embodiments, the soft actuators can be different sizes and/or the soft actuators actuate at different pressures and/or the soft actuators are different materials.

In any of the preceding embodiments, the soft actuator can include embedded electronics configured for measuring tissue impedance (e.g. the health of tissue after cauterizing) or electro-chemical sensing for medical diagnostics (e.g. determining ion levels) or the electronics power LEDs to improve visibility.

In another aspect, the soft material retractor includes at least one soft actuator, the soft actuator comprising at least one pressurizable interior space, wherein the retractor comprises a first flexible resting state and a second stiffer pressurized state; and an anchor for securing the soft actuator against a soft body component in a patient.

In one or more embodiments, the soft actuator bends upon fluid pressurization, or the soft actuator extends upon fluid pressurization.

In one or more embodiments, the soft actuator displaces soft tissue or anatomical structures, and for example, fittings, like hooks, are adapted to the actuator to improve connection to anatomical features, wherein the fitting optionally is attached to the distal end of the actuator and is configured to anchor to soft tissue or bony features such as the lesser sciatic notch.

In one or more embodiments, the fitting has a vacuum connection to suction onto anatomical features.

In one or more embodiments, the anchor includes suction cups for grabbing or anchoring to anatomical structures.

In one or more embodiments, the anchor includes surgical nails, staples, barbs, or screws for grabbing or anchoring to anatomical structures.

In one or more embodiments, the anchor further includes a handle secure to the soft actuator.

In one or more embodiments, the soft actuator further includes a lumen, and for example, the lumen is configured for one or more of delivering therapies, sample collection, insertion of objects, suction, intubation and medical diagnostic sensors.

In one or more embodiments, the retractor is sized for use as a deep pelvic retractor.

In one or more embodiments, the soft retractor further includes electronics embedded in the soft actuator, and for example, the embedded electronics are configured for measuring tissue impedance (e.g. the health of tissue after cauterizing) or electro-chemical sensing for medical diagnostics (e.g. determining ion levels) or the electronics power LEDs to improve visibility.

In any of the preceding embodiments, functional materials can be incorporated into the soft actuator.

In another aspect, a soft material retractor includes a first retractor as described herein configured to hold open an incision, and a second retractor as described herein secured to the first retractor and configured for insertion into an incision to displace anatomical structures.

In one or more embodiments, the second retractor can be positioned along a perimeter of the first retractor.

In one or more embodiments, illumination devices can be integrated into the soft material retractor.

In one or more embodiments, an RFID reader can be integrated into the soft material retractor.

In another aspect, the use of a soft tissue retractor is provided using a soft material reatractor as described herein to hold or reposition an organ of a patient.

In another aspect, the use of a soft tissue retractor is provided using a soft material retractor as described herein for holding an incision or wound open.

BRIEF DESCRIPTION OF THE DRAWING

The following images detail multiple embodiments and applications. The invention is described with reference to the following figures, which are presented for the purpose of illustration only and are not intended to be limiting. In the Drawings:

FIGS. 9A-9D depict exploded and assembled view of soft actuator components of the inactive and active states, in which FIG. 9A is a soft bending actuator; FIG. 9B is a bend-twist soft actuator; FIG. 9C is a linearly extending soft actuator; and FIG. 9D is an extend-twist soft actuator.

DETAILED DESCRIPTION

A retractor is a surgical instrument used to separate the edges of a surgical wound or incision or to hold back underlying organs and tissues so that body parts under the incision can be accessed. In one embodiment, a soft bodied retractor for use in holding an incision open is described. In another embodiment, a soft bodied retractor for use in positioning internal organs is described. Because the retractor is soft and of the same modulus generally as the tissues and internal organs with which it interacts, e.g., Young's modulus <10 MPa (as least compared to the modulus of metal), the device is safer to use and less likely to inflict damage in use.

In one aspect, the soft retractor includes at least two soft actuators that are responsive to fluid pressurization. The actuators are spaced apart from each other by a distance, D, that is maintained by a flexible sheet spanning the actuators. The flexible sheet can be, for example, a thin plastic sheet or co-molded rubber. Distance D can be selected to span a wall thickness of the body cavity in which the retractor is to be used. For example, to hold open an incision, the distance D can be in the range of a few millimeters to centimeters, where variability derives in large part from a patient's subcutaneous tissue thickness (body fat), which can be as much as three cm or more. Distance may also be determined by the amount of tissue or anatomical structures that must be displaced inside the body. For example, in situations where a surgeon desires a clear path or line of sight to a target area, such as viewing the gall bladder while inside the rib cage, the D between the two or more actuators may be on the order of 10s of centimeters. In certain embodiments, the actuators are substantially parallel to one another. In other embodiments, the actuator spacing can vary along the length of the actuator. Non-parallel spacing can be useful when the cavity wall thickness varies, for example, when the fascia, muscle, fat, etc. around the cavity is of different thickness. The actuators can be of the same shape and/or size and or material; or the size and/or shape and/or material of the actuators can be different. The actuators can be actuated by fluidic pressures, e.g., gas and liquid pressurization. The pressures used to actuate the actuators can be the same or different.

Figure 1A:
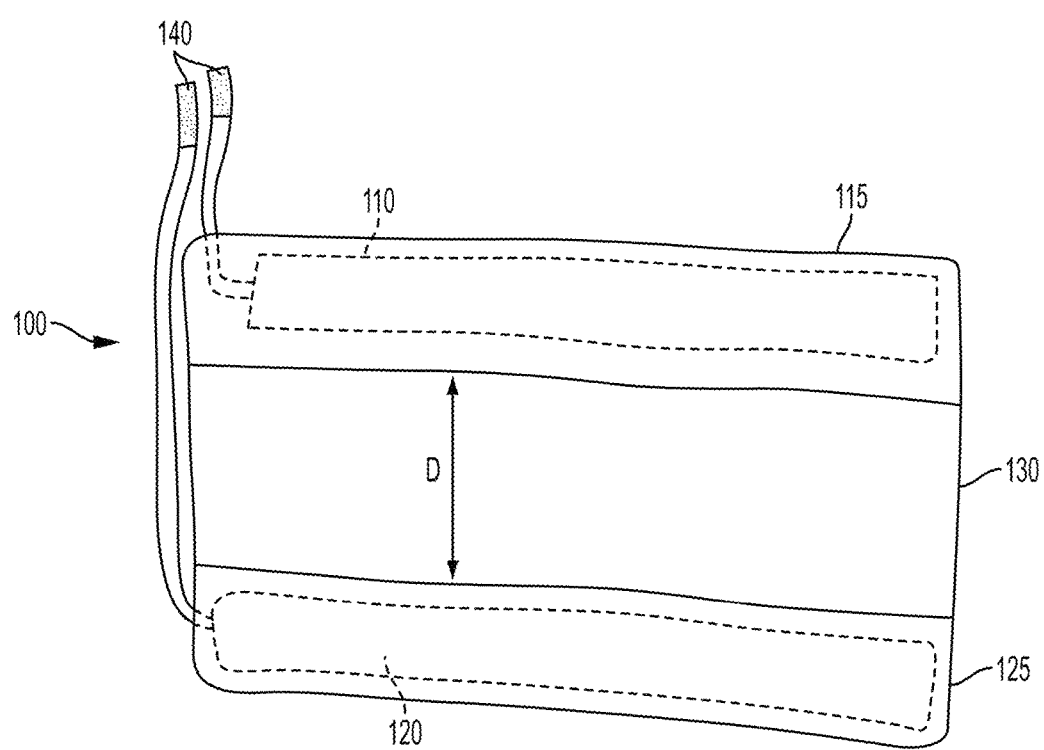
FIG. 1A presents a side view of an unpressurized tissue retractor according to one or more embodiments.

FIG. 1A is a schematic illustration of a soft bodied retractor 100 according to one or more embodiments. The figure shows two soft bending actuators 110, 120 that run substantially parallel to one another. The actuator can be a finger actuator capable of bending on pressurization. A soft bodied finger actuator can be used. In this particular embodiment, the actuators are housed in flexible sheaths 115, 125 that is attached to a flexible sheet. The flexible sheet defines a spacing D between the two actuators. The flexible sheet can be a medically accepted plastic or other soft material and the sheath can form a thermal bond with the flexible sheet to secure the actuators to the sheet. Other modes of securing the sheath to the sheet are contemplated, such as gluing, stitching, co-molding and the like. In other embodiments, the two actuators can also be connected using a number of shorter flexible connectors attached along the length of the actuator as is shown in FIG. 5. The actuators are connected to fluid lines 140 for pressurization, and can be attached to separate or the same pressurization sources. FIG. 1A shows the actuator connected to separate fluid lines, but they can also be connected to a single pressurizing source so that the actuators can be actuated together.

Figure 1B:
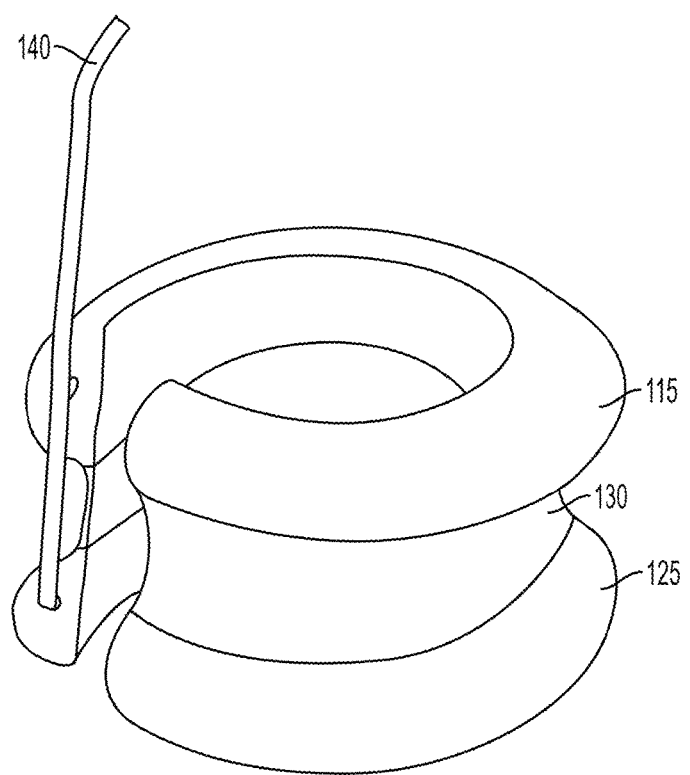
FIG. 1B depicts the tissue retractor of FIG. 1A in a pressurized state where the two bending actuators curl to form a tubular shape.

In some embodiments, when pressurized, the actuators bend to form a rigid curved, e.g., C-shaped, body. The flexible sheet limits the separation between the two actuators. FIG. 1B is an illustration of a pressured and actuated soft retractor according to one or more embodiments. The two bending actuators have curled into a C-shape and the actuators stiffen under pressurization. In other embodiments, when pressurized, the actuators extend linearly. See, for example, FIGS. 5A-5C.

The retractor can be used for example to hold the incision walls apart and to maintain the incision opening in a stable shape and size. In use, the soft retractor can be inserted in an unactuated state into an incision and positioned so that one actuator is located inside the incision and the other is located on the surface of the patient. The actuators are flexible in the unactuated state, which allows them to be easily located and manipulated in the incision. The actuators are then pressurized so that the actuators bend into a C-shape or O-shape or other shape that helps maintain the incision opening. The surface spanning the two actuators holds back tissue, fat, fascia and other organs to keep the incision open. The actuators curl to open the incision where the thin film supports this by holding back the fascia layer (e.g., skin, fat, muscle, etc.).

In one embodiment, the actuators are straight before actuation and bend upon actuation into the shape that holds the incision open. In other embodiments, the actuator is curled before actuation and the actuator straightens or elongates on actuation. In this case, the incision site serves as a mechanical form and the actuator presses against the incision as it elongates and forces the actuator into a C-shape or O-shape.

In one or more embodiments, it can be desired to vary the spacing D between the actuators, for example, to adjust for varying thicknesses of the fascia layer among patients or among different tissue types. The spacing D can be adjusted in a number of ways. For example the distance D can be increased by stretching and/or plastically deforming the flexible cover. In other embodiments, the flexible sheet can be rolled around one or both of the actuators and the flexible sheet can be rolled or unrolled to attain the desired spacing. The sheet can be secured in the desired location using a clip, tape, hook or loop fabric, adhesive tape or other securing means. In still other embodiments, the flexible sheet can be made in two parts, and the edges can be fitted with an adjustable adhesive band that can be adjusted to enlarge or reduce the film size.

Figure 2A:
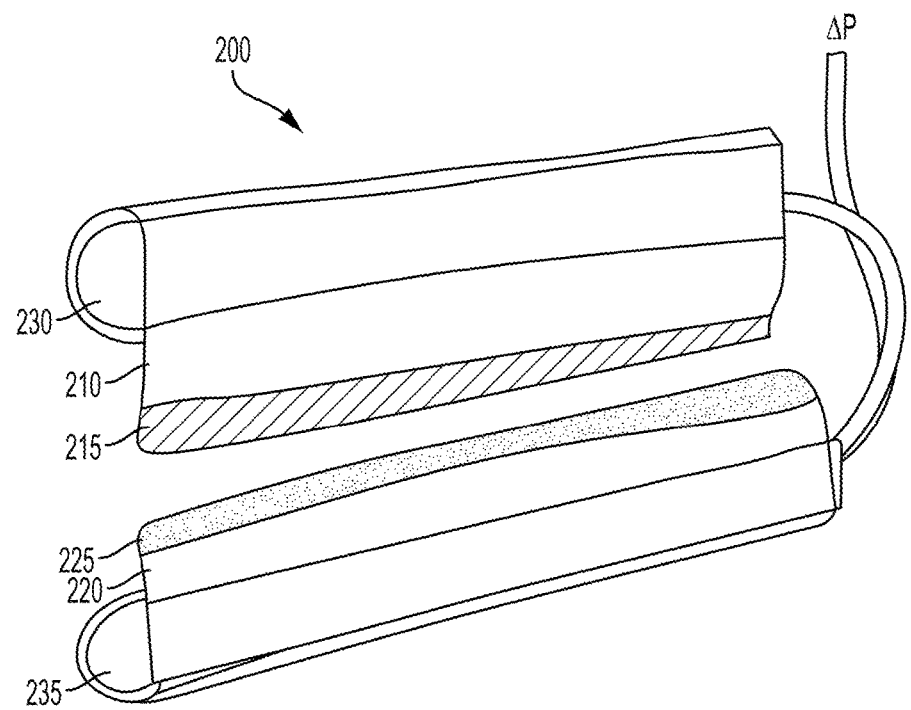
FIG. 2A presents isometric view of a self-retaining incision site retractor where the distance between the actuators can be adjusted according to one or more embodiments.
Figure 2B:
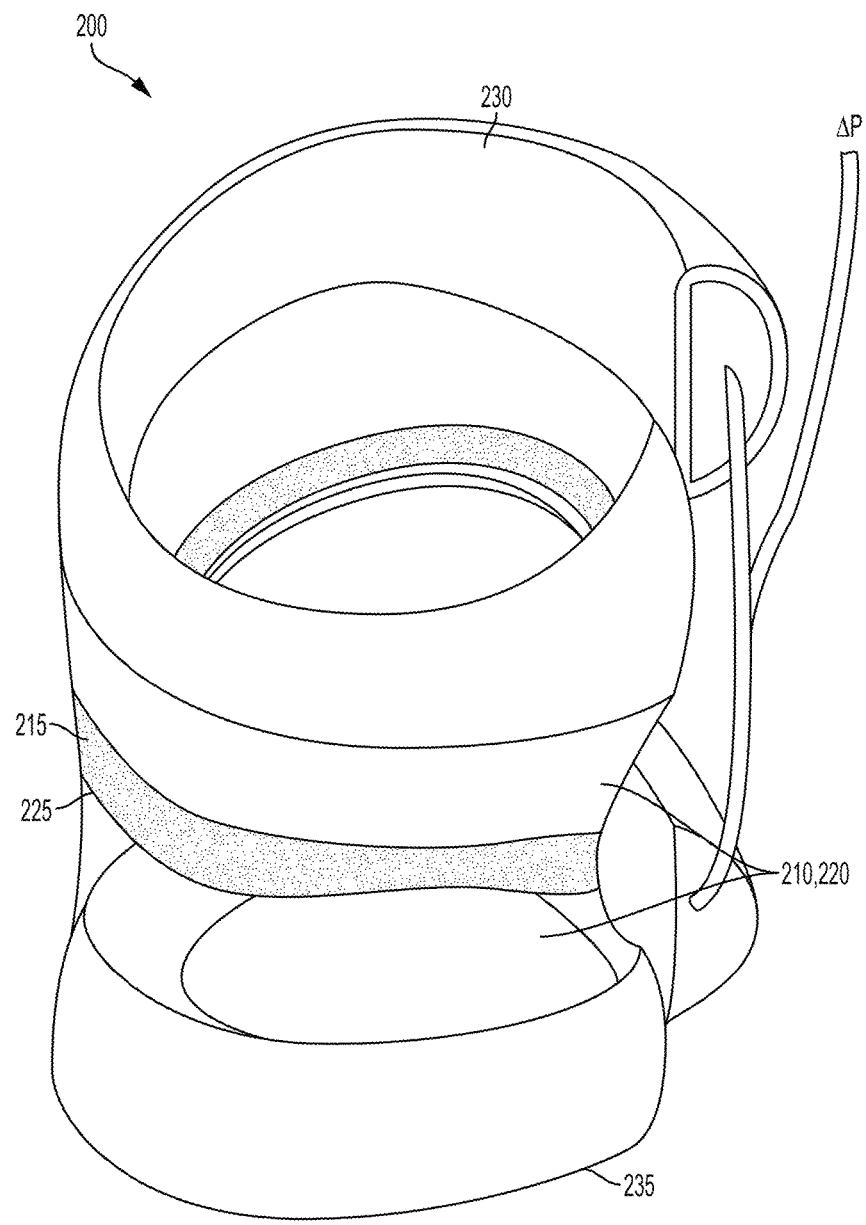
FIG. 2B presents the self-retaining incision site retractor in FIG. 2A under pneumatic or hydraulic fluid pressurization.

FIG. 2A presents a view of another self-retaining incision retractor 200 according to one or more embodiment, in which the distance between the actuators can be adjusted. FIG. 2B presents the incision or wound retractor in FIG. 2A under fluid (hydraulic or pneumatic) pressurization, where like elements are similarly labeled. It should be noted that all examples of "incision" retractors in this document could also be applied to the retraction of wounds or trochars.

In this example, the flexible sheet is separated down the length with one side 210 having a 'hook' feature 215 and the other side 220 a 'loop' connection 225. Each side 210, 220 houses one of the two actuators 230, 235. This feature is designed to accommodate the range of fascia thicknesses that patients may present (e.g., obese and thin patients will have very different fascia thicknesses). For example, for an obese patient the separation distance can be adjusted to as far as is physically allowable along for the hook and loop, e.g., Velcro® adhesive strips. For patients with thinner fascia layers the actuators can be positioned closer together. Hook and loop is presented as one reversible and adjustable connective means, but other connective mechanisms can be used such as zip ties, cable, adhesive strips, and etc.

In one or more embodiments, an extra sheet is included to provide extra length. For example, a first sheet includes the first actuator and a first adhesive edge, a second sheet includes the second actuator and a second adhesive edge, and a third sheet is disposed between the first and second sheet and includes opposing adhesive edges for adhering to the adhesive edges of both the first and second sheets.

Figure 3A:
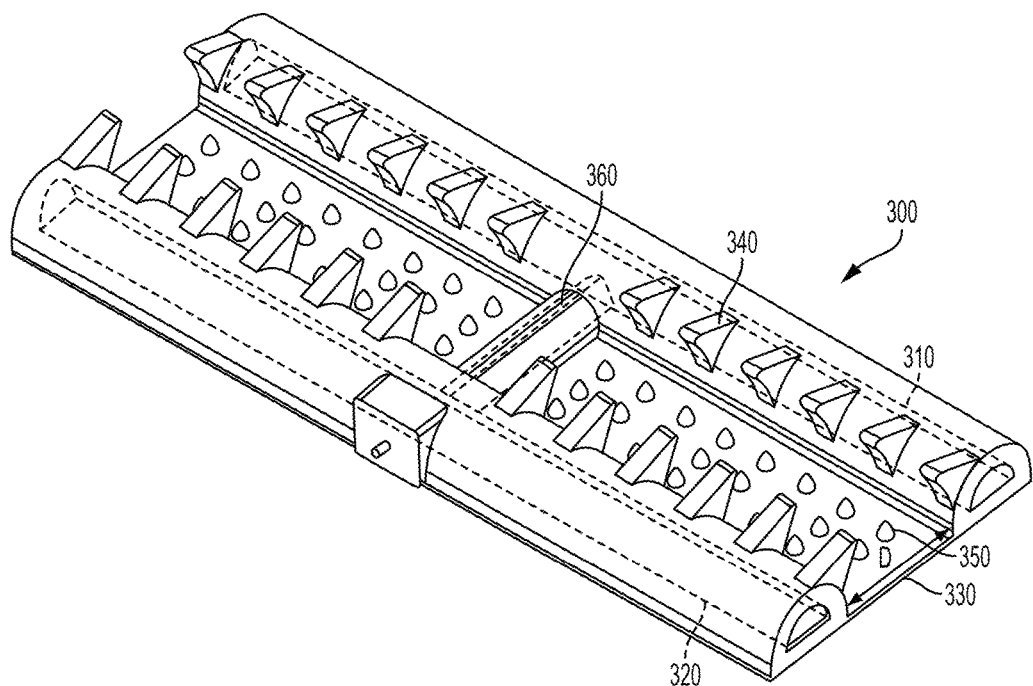
FIG. 3A presents an embodiment of the tissue retractor, where a thin layer of elastomeric material (e.g., silicone) is molded over the soft actuators and is used as the material to bridge the distance between the actuators according to one or more embodiments.

In one or more embodiments, the soft retractor can be molded from an elastomer. In this embodiment, an elastomer is used to form a bridge between the two actuators instead of the soft plastic spacer. FIG. 3A illustrates this embodiment of the tissue retractor where a thin layer of elastomeric material (e.g., silicone—although other elastomers such as urethane based elastomers are also suitable) is molded over the soft actuators and is used as the material to bridge the distance between the actuators. As in the embodiment shown in FIG. 1A, the retractor 300 includes actuators 310, 320, spaced apart from one another with a flexible sheet 330 spanning the distance D.

In FIG. 3A, a finger actuator can be embedded in a thin layer of elastomer. By forming the soft retractor out of a molded elastomer, it is possible to introduce additional features and functionalities in the device. For example, soft teeth-like features can be molded into the device to enhance stability when retracting tissue and to provide more contact points for locking onto the skin. Protruding fingers 340 along the actuator and projections 350 along the spacing surface between actuators can be molded to assist in placing and securing the device during use. In addition, it is possible to mold a channel 360 between actuators so that a single pressurizing source can be used.

Figure 3B:
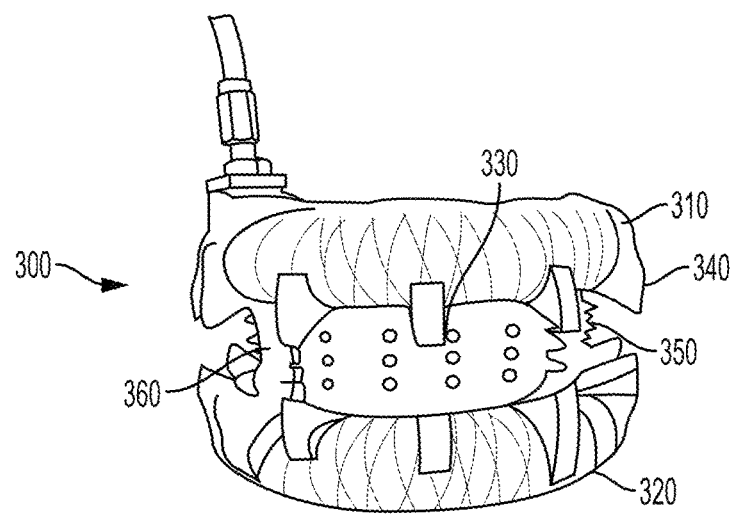
FIG. 3B is a photograph of a tissue retractor according to FIG. 3A in a pressurized state.
Figure 3C:
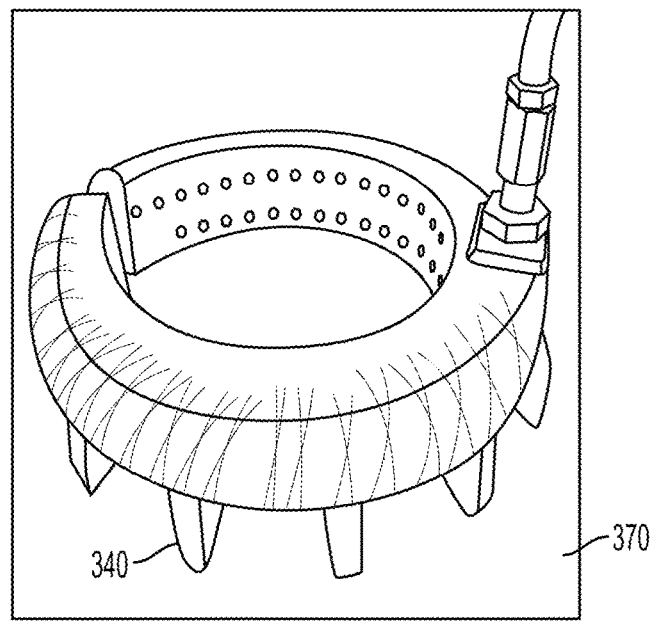
FIG. 3C depicts the pressurized self-retaining tissue retractor in FIG. 3B in a foam skin model.

FIG. 3B is a photograph of the molded soft retractor in a pressurized, actuated state, where like elements are similarly labeled. The securing protrusions on both the actuator 340 and the spacer wall 350 can be seen in this figure. FIG. 3C shows a side view of the soft retractor in use. A foam sheet 370 is used to mimic a patient skin and the images show that the soft retractor is capable of insertion and placement in a model incision. Securing protrusions 340 are shown locked into the model foam 'skin' and demonstrates the ability of the features to stabilize the retractor when in use. The soft retractor can hold the incision open.

Figure 4A:
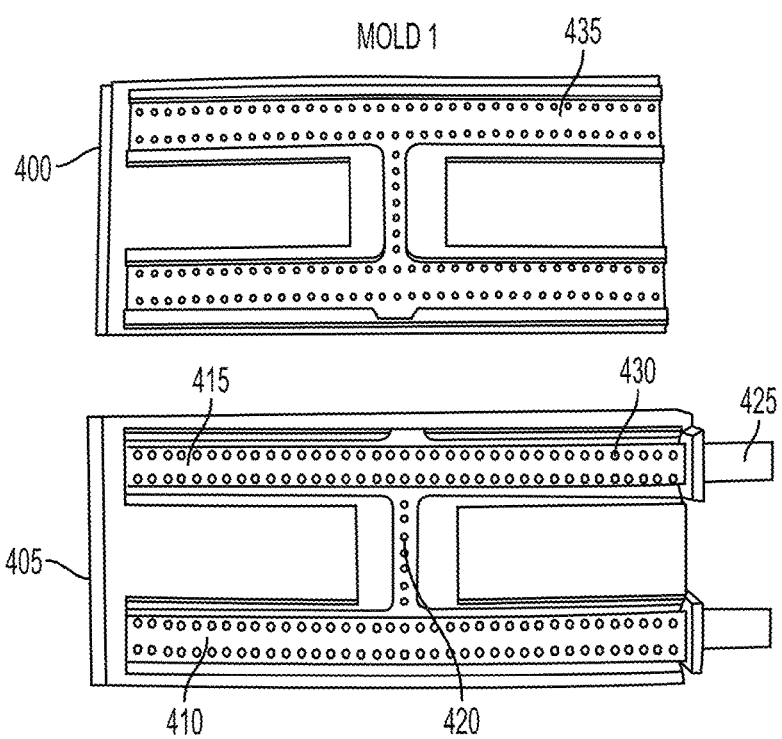
FIG. 4A depicts the first molding step in a two-step molding process for the fabrication of a tissue retractor according to one or more embodiments.

FIGS. 4A-4D illustrate a method of making the molded soft retractor shown in FIG. 3A. FIG. 4A depicts the first step where the two soft actuators are formed and molded together with bridge connection that connects their bladders. FIG. 4A shows the upper mold 400 and lower mold 405 used in a molding manufacture of the tissue retractor in a two-step molding process. The molded body, including two elastomeric actuators 410 and 415 integrally connected through a bridging channel 420, is shown in the lower mold. A lower durometer rubber is preferred for molding the soft actuators. The actuator can be a simple tube actuator and the interior channel can be formed, for example, by using a rod 425 to define the inner space of the actuators. In additions, protrusions 430 can be introduced on the outer surface of the soft actuator mold to increase surface area of bladder to improve the bond strength with the next layer of rubber. Upper mold 400 shows depressions 435 in the mold used to form the protrusions.

Figure 4B:
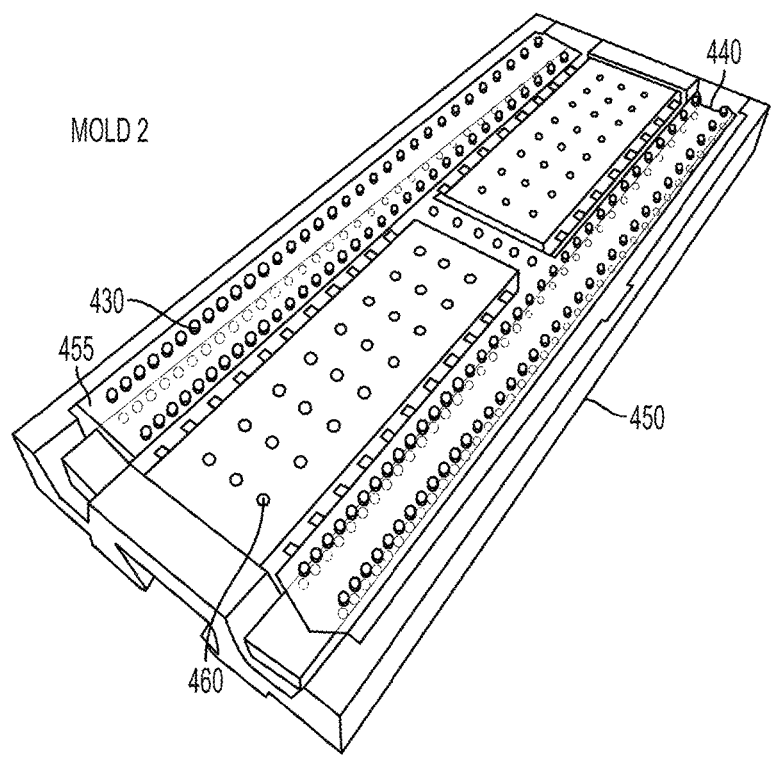
FIG. 4B depicts the molded part from Mold 1 that is transferred and repositioned in Mold 2.
Figure 4C:
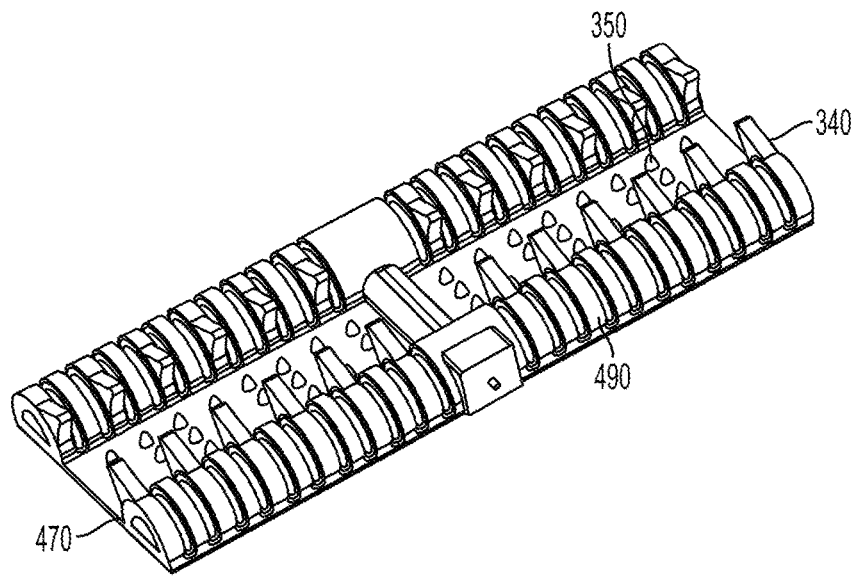
FIG. 4C is an illustration of the rubber reinforced self-retaining tissue retractor demolded from Mold 2 with the ends capped.
Figure 4D:
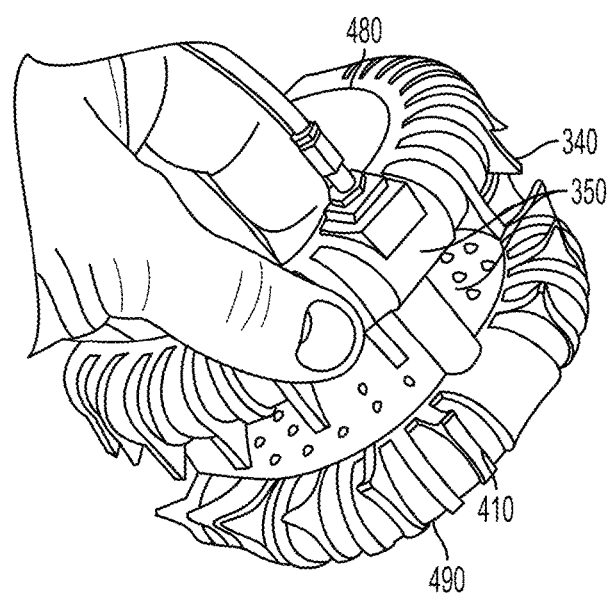
FIG. 4D is a photograph of a rubber reinforced self-retaining tissue retractor according to FIG. 4C in a pressurized state.

Referring now to FIG. 4B, the molded part from Mold 1 440 is transferred (including spacer rods) to Mold 2 450. This mold contains cavities 455 that define the stain limiting features that create the anisotropies that cause the actuator to curl. It is preferred that a higher durometer rubber fills these cavities (though inextensible fiber reinforce composite sheets would also be suitable). These cavities can also define the shape of the protruding features 340 shown in the device of FIG. 3. Recesses 460 can be used to create the protruding features 350 of the device illustrated in FIG. 3. The assembled mold before casting is shown in FIG. 4B. Once molded, the ends of the molded body are sealed with soft elastomer to create the soft retractor. FIG. 4C is an illustration of the device demolded from Mold 2 with the ends 470 capped. FIG. 4D depicts the rubber reinforced device in a pressurized state. Protrusions 340, 350 on the spacer wall and the actuators are clearly seen.

The actuator can be any actuator that pressurizes into a stiffened shape on actuation. By way of example, the actuator can be a balloon or bladder that inflates into the desired shape. The actuators can be made of soft material of low modulus that forms a bladder or chamber that bends or extends upon pressurization into the desired shape. In one or more embodiment, the actuator can be a pneumatic network of chambers, it can pleated or folded and capable of expansion; or it can be in the form of a bellows.

In one or more embodiments, the bladder can be a finger actuator that has a flexible extensible side and a strain limiting side. The bladder bends around the strain limiting side on pressurization. In other embodiments, the actuators can be extending actuators designed to extend linearly when actuated. Linearly extending actuators can also be made up of a flexible extensible materials and a strain limiting layer. The strain limiting layer can be a fiber reinforced layer or it can be a stiffer elastomer than the extensible layer or it can be an embedded sheet material. In one or more embodiments, the extensible layer is under compression in its resting state and the fluid pressure unbends and linearly extends the actuator. See, WO 2012/148472, published Jul. 28, 2013, and entitled "Soft Robotic Actuators"; Ilievski F, Mazzeo A, Shepherd R, Chen X (2011) "Soft robotics for chemists", Angew Chem Int Ed Engl 50:1890-1895; and Shepherd R, Ilievski F, Choi W, Morin S, Stokes A, Mazzeo A, Chen X, Wang M, Whitesides G (2011) "Multigait soft robot," Proc Natl Acad Sci USA. 2011 Dec. 20; 108(51): 20400-3, for further details on soft bending and extending actuators, the contents of which are incorporated by reference.

Figure 9A:
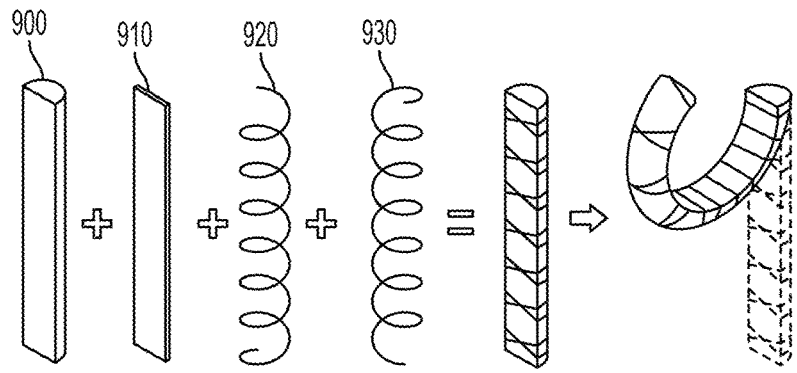

Some of the soft actuators presented in this work are composite constructions that consist of an elastomeric bladder that deforms in response to fluid pressurization and anisotropic reinforcements in its wall that determine the deformation. By reinforcing the walls of the bladder, it is possible to mechanically program the actuator to perform a range of motions under fluid pressurization including bending, extending, extend-bend, and extend-twist. FIG. 9A illustrates the components that can be used to assemble a fiber-reinforced soft bending actuator, which consists of a elastomeric bladder 900, e.g., actuators 410, 415 in FIG. 4A. A strain-limiting layer 910 can be an inextensible fiber reinforce composite sheets introduced as inextensible sheet along a portion of the actuator mold; the sheet can be woven or non-woven fabric or paper or open web or oriented fibers that permit flow of elastomer in and around the strain limiting feature during the molding process to embed the strain limiting layer in the composite sheet. Alternatively, as discussed below, the strain limiting layer can be a higher durometer polymer extending along one portion of the actuator length. The strain-limiting layer promotes bending by inhibiting linear growth along a portion of the bladder. Symmetric arrangements of radial reinforcements including clockwise arrangement of string 920 and/or counterclockwise arrangement of string 930 can be used to limit radial expansion. The string can be wound around the molded bladder after it is removed from the first mold.

Figure 9B:
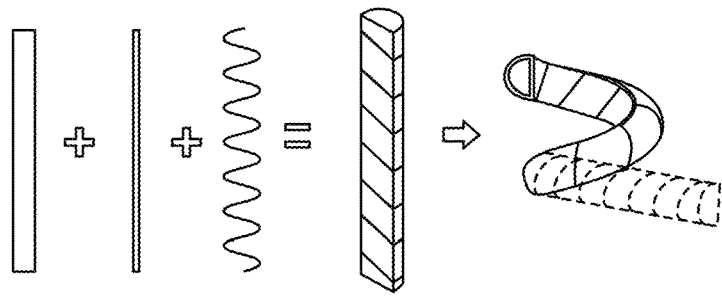
Figure 9C:
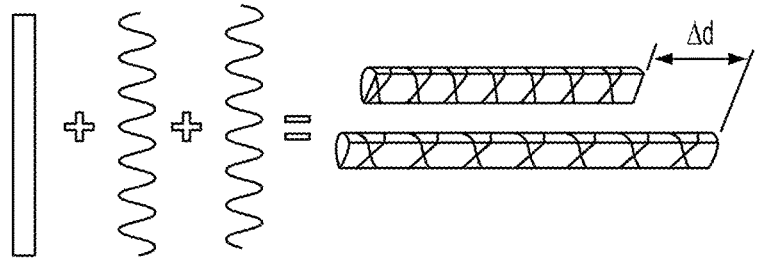
Figure 9D:
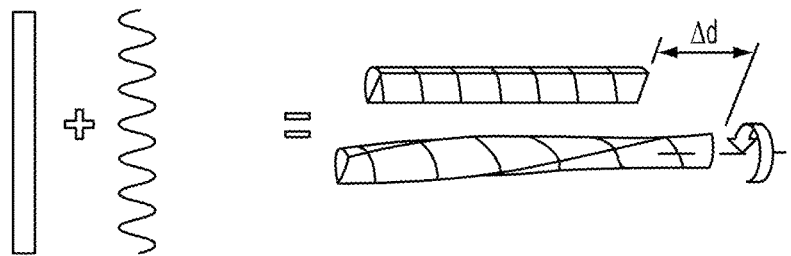

FIG. 9A presents the component to assemble a fiber-reinforce extending actuator, which consists of a symmetric arrangement of radial reinforcements to limit radial expansion. The other class of programmable motions—extending, extend-twist, bend-twist—are created by adjusting the combination of the radial reinforcements (FIG. 9B-9C).

Figure 10A:
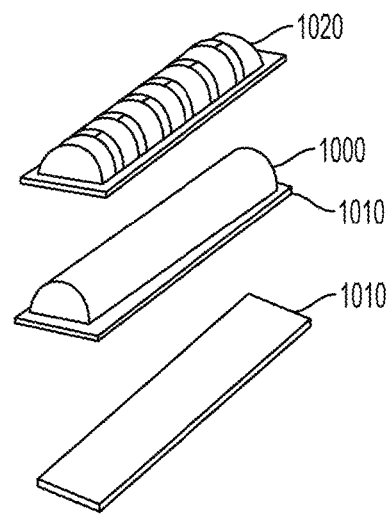
FIG. 10A depicts an exploded view of a molded actuator illustrating the strain limiting features and the radially limiting features surrounding a bladder.
Figure 10B:
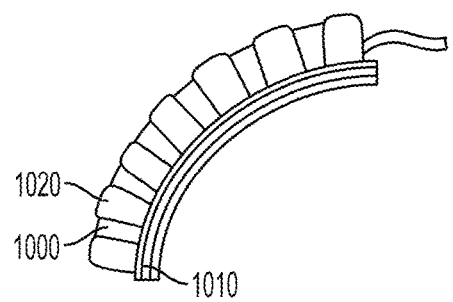
FIG. 10B depicts the actuator components FIG. 10A assembled and the actuator pressurized.

In other embodiments, both the strain limiting feature and the radially limiting feature can be part of molded high durometer material. FIG. 10A illustrates the actuator components, including a bladder 1000, strain limiting layer 1010, which can be a high durometer material or a reinforced composite sheet as described above and a radially limiting feature 1020, which can also be made of a material having a higher durometer than the bladder. FIG. 10B illustrates this combination of elements to provide bending actuation. The bladder 1000 is bounded on the lower surface 1010 by a strain limiting layer made up of a high durometer material. The upper layer 1020 provides bands of radially constraining high durometer material. See, also FIG. 4B, in which bands 490 serve as the radially limiting elements.

In other embodiments, the tissue retractor can be made with linear actuators having connectors on the ends that allow the ends to be coupled. By 'linear actuator', it is meant a pressurizable device that increases in length upon actuation.

Two actuators can be connected with a flexible sheet that is capable of extension or stretching in the direction of actuator extension or it can be connected along its length with shorter sections of flexible material that can accommodate actuator linear extension. The ends can be connected to form a circle and the actuators can be pressurized to stiffen the actuator. The stiffened actuator increases in length, which translates into an increase in diameter that can be used to generate and outward force that holds back soft tissue.

Figure 5A:
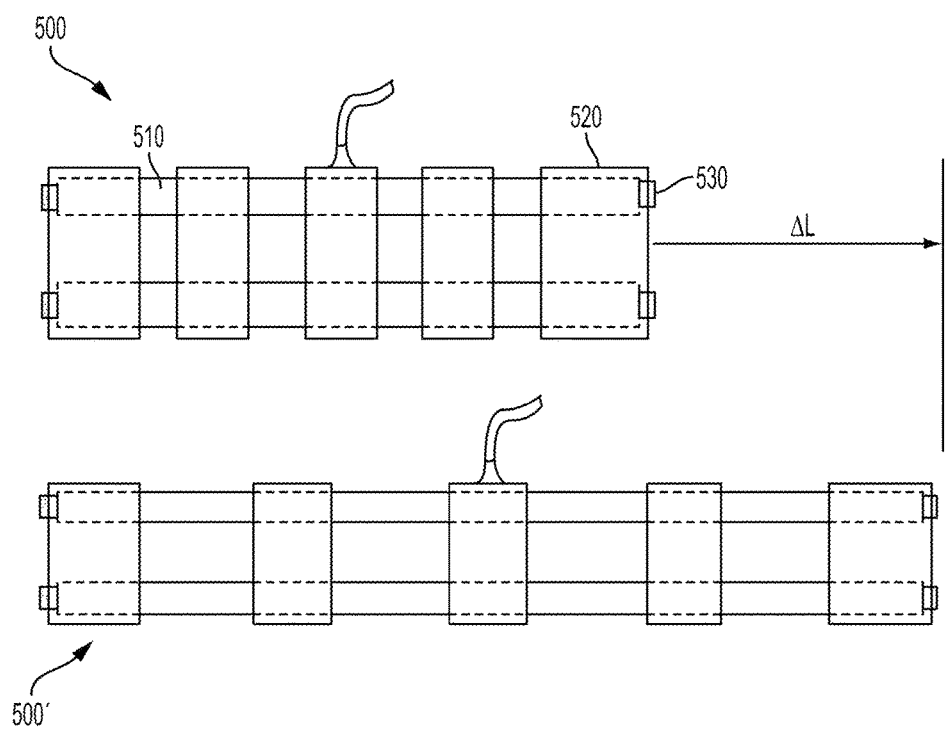
FIG. 5A depicts a tissue retractor with linear extending actuators in parallel that are connected by a flexible covers in its resting state (upper) and pressurized state (lower) where the device has grown in length.

FIG. 5A depicts a tissue retractor 500 with linear extending actuators 510 in parallel that are connected by a flexible covers 520 (e.g. thin plastic or co-molded rubber). The ends of the actuators have connectors 530 (e.g. magnetic, snap, hook and loop, etc.) that enable the actuator to be connected end-to-end. It should be noted that these connectors can be used to connect multiple actuators in series. The ability to connect multiple actuators allows the user to obtain soft tissue retractors of different diameters, making it versatile and able to be used with a range of incision sizes. The lower image in FIG. 5A depicts the tissue retractor in a pressurized state 500' where the device has grown in length, ΔL.

Figure 5B:
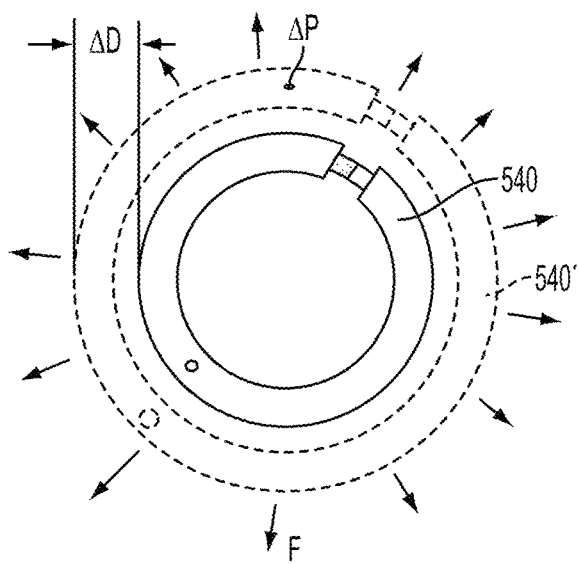
FIG. 5B demonstrates that the tissue retractor can be connected end-to-end to form a close loop.
Figure 5C:
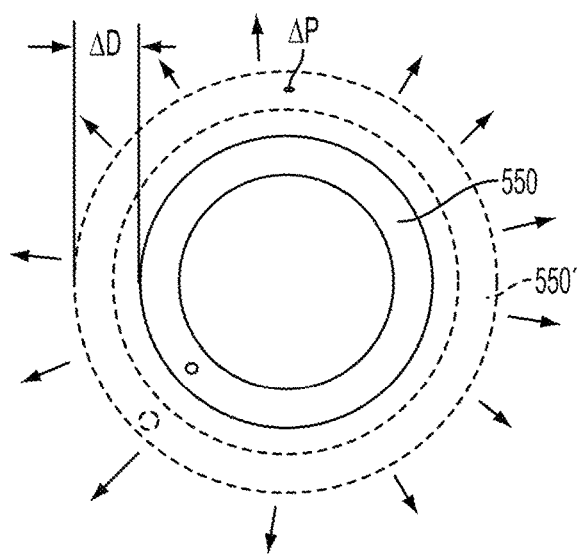
FIG. 5C illustrates another embodiment of FIG. 5B where the device in its initial fabricated shape is a closed loop.
Figure 6A:
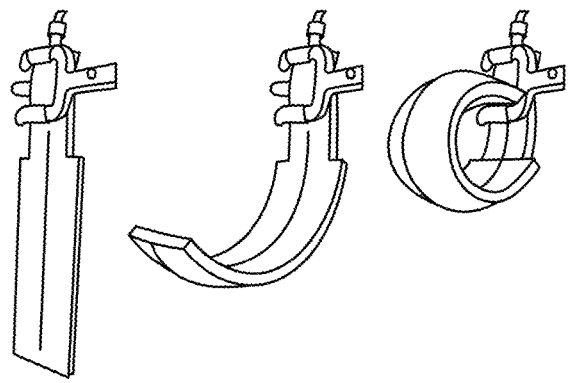
FIG. 6A depicts an elastomeric bending actuator at (left) no pressurization, (middle) partial pressurization, (right) full pressurization for use in coordination with a tissue retractor according to one or more embodiments.

FIG. 5B demonstrates that the tissue retractor 540 can be connected end-to-end to form a closed loop. When the device is pressurized it grows in diameter to occupy position 540' and generates radial forces that can be used to displace soft tissue, anatomical structures (e.g. stomach, intestines, improving access to gall bladder, etc.), and etc. It should be noted that, while not pictured, the actuators could be molded and/or pressurized to be at different diameters for making conical openings. FIG. 5C illustrates another embodiment of FIG. 5B where the device 550 in its initial fabricated shape is a closed loop. This loop can be made in a variety of shapes during the molding process including circular, diamond, or fisheye shaped. When the device is pressurized it too grows in diameter to occupy position 550' and generates radial forces that can be used to displace soft tissue, anatomical structures In another aspect, soft actuators can be used as paddles or organ retractors for moving or displacing an organ or tissue in the body cavity. FIG. 6A depicts an elastomeric bending actuator that is capable of bending. The bending motion can be used to move or displace an organ or tissue in the body cavity. FIG. 6A shows the soft actuator at (left) no pressurization, (middle) partial pressurization, (right) full pressurization. The soft bodied characteristics of the device help to reduce damage and trauma to the sensitive internal organs. Soft actuators useful as soft retractors and their mechanism of operation and manufacture have been previously described. See, e.g., WO 2012/148472, published Jul. 28, 2013, and entitled "Soft Robotic Actuators"; Ilievski F, Mazzeo A, Shepherd R, Chen X (2011) "Soft robotics for chemists", *Angew Chem Int Ed Engl* 50:1890-1895; and Shepherd R, Ilievski F, Choi W, Morin S, Stokes A, Mazzeo A, Chen X, Wang M, Whitesides G (2011) "Multigait soft robot," *Proc Natl Acad Sci USA*. 2011 Dec. 20; 108(51): 20400-3, which are incorporated in their entirety by reference. In one or more embodiments, the soft retractor can be radiopaque for interval visualization and can include, for example, radiopaque markers. In one or more embodiments, a radioopaque additive is mixed into the material that makes up the soft actuator.

Figure 11A:
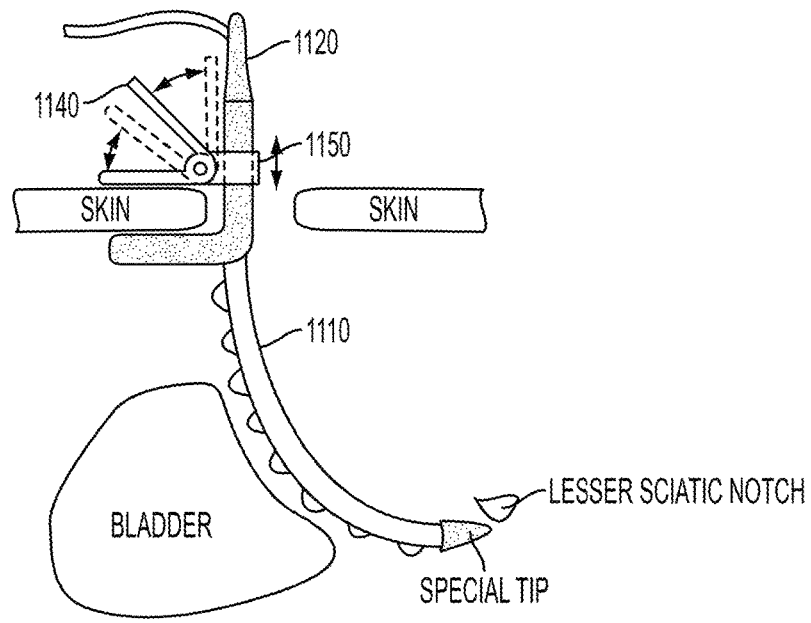
FIG. 11A depicts a spring clamp attached to the handle of the retractor where the spring clamp is used to anchor the retractor according to one or more embodiments.
Figure 11B:
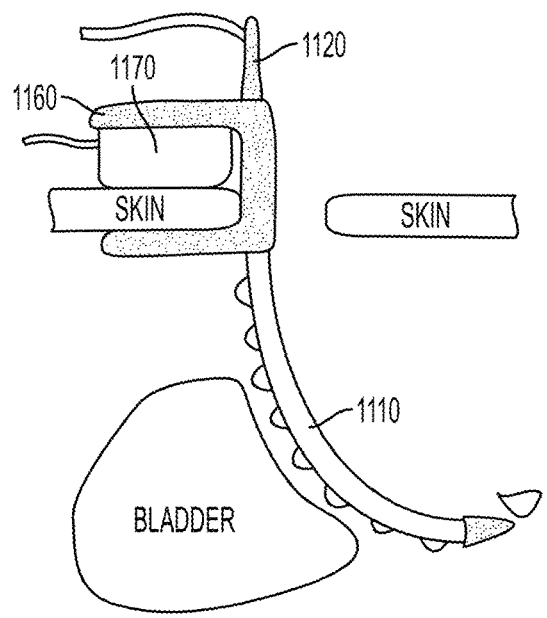
FIG. 11B depicts an inflatable bladder used to anchor the handle of the retractor according to one or more embodiments.

When used as a soft retractor in this way, the soft retractor can be equipped with a handle on one end that allow medical professionals to position the retractor relative to the tissue it displaces. In one or more embodiments, the soft tissue retractor can also include an anchoring mechanism that assists in positioning and securing the device in the body cavity. The anchoring mechanism can include the protrusions described herein above. The anchoring mechanism can also include clamping mechanisms or clamping surfaces integrated into the end proximal to the soft retractor handle. FIG. 11A depicts a paddle actuator 1110 such as that shown in FIG. 6A secured to handle 1120. A spring loaded lever 1140 is integrated into the handle of the retractor. The claim incudes has an adjustable base 1150 movable along a shaft of the handle to adapt to a patient's skin thickness. When in place, the device clamps to the skin to anchor the proximal end of the soft retractor. FIG. 11B depicts an alternative embodiment, in which clamp 1160 is provided integral to handle 1120. The retractor is secured by inflating bladder 1170 to clamp the skin inside the U-shaped structure 1160. Alternatively, these anchoring methods, and other methods known to those skilled in the art, can be used to clamp the proximal end of the retractor to structures outside the body such as to a rigid structure in the operating room (e.g. the table), to a robotic arm, to the operator, or adhered to skin. The soft retractor can also include an anchoring mechanism or feature at the end distal to the handle that can anchor to soft tissue or boney features via suction, staples, barbs, or screws. See, e.g., FIG. 7D.

Figure 6B:
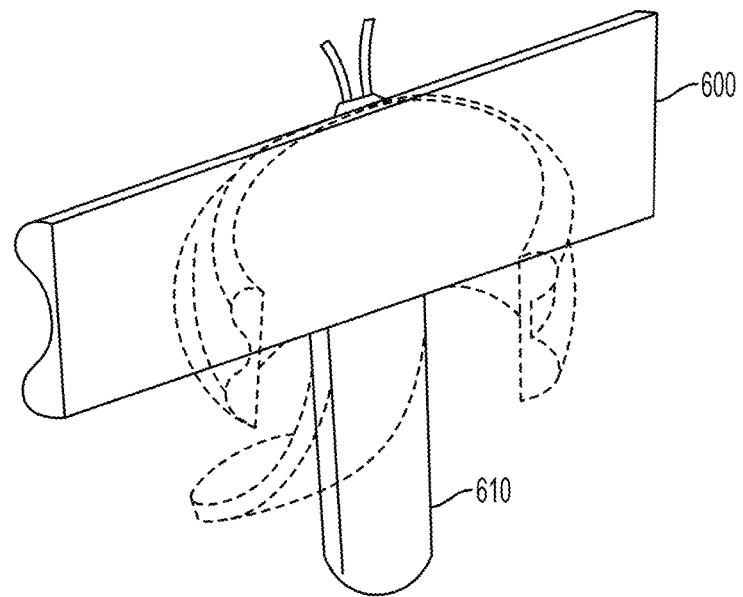
FIG. 6B depicts a tissue retractor and a deep pelvic retractor combined into a single device according to one or more embodiments.

In another aspect, the soft tissue retractor can be equipped with a paddle actuator that can be used to gently move organs or tissue while holding open an incision. FIG. 6B depicts a tissue retractor 600 and an organ retractor 610, e.g., a deep pelvic retractor, combined into a single device. In this illustration the solid line depicts the device in its unpressurized state. The dashed line depicts an example of a pressurized state. Two pneumatic lines may be included so that each retractor can be controlled separately. It should be noted that more actuators can be incorporated to apply forces in other directions. In addition, a handle (not shown) can be attached to help position the deep pelvic retractor.

Figure 7A:
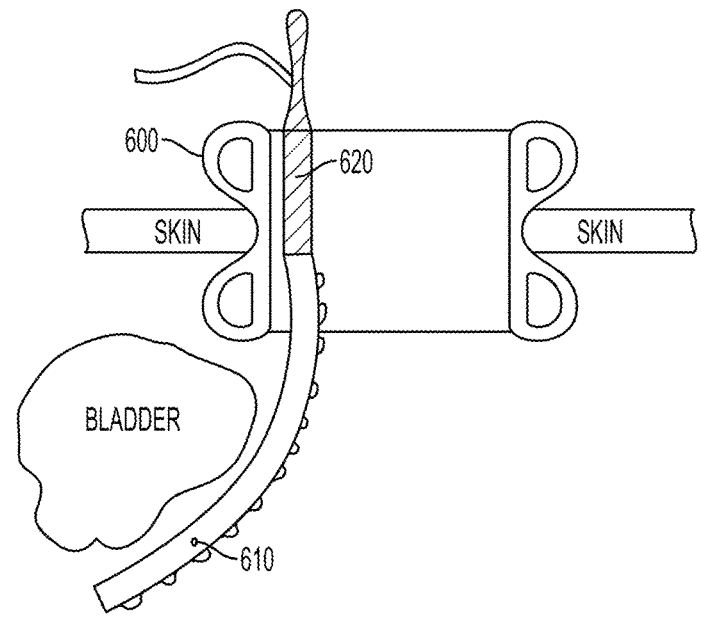
FIG. 7A depicts the elastomeric bending actuator (working in conjunction with the tissue retractor) passing through an incision and displacing anatomical features (e.g. bladder, etc.).

FIG. 7A depicts the elastomeric bending actuator 610 (working in conjunction with the tissue retractor 600) passing through an incision and displacing anatomical features (shown here for example as a bladder). Handle 620 can be used to position bending actuator 610. When used in this way, the device is suitable for use as a deep pelvic retractor (DPR). In this embodiment, the soft tissue retractor both holds the incision site open and serves as an anchoring point for the deep pelvic retractor. The two features can be separately pressurized for independent operation.

Figure 7B:
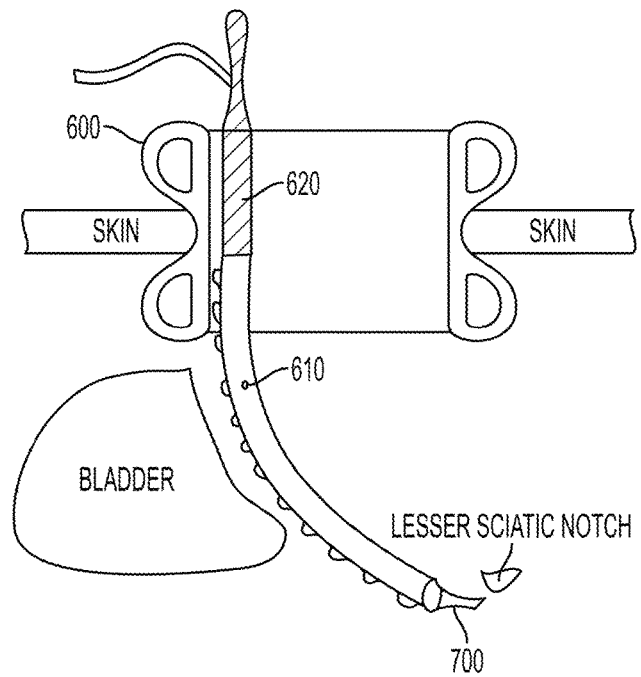
FIG. 7B depicts a deep pelvic retractor with a different orientation and a special tip for anchoring to other anatomical features according to one or more embodiments.

FIG. 7B depicts the deep pelvic retractor with a different orientation and a special tip 700 for anchoring to other anatomical features. In this example, a special tip can be added to the deep pelvic retractor that allows the device to use the lesser sciatic notch or other bony prominences as an anchoring point. The tip can be equipped with a vacuum connection for generation of suction that improves attachment to an anatomical feature. It should be noted that a linearly extending actuator could be used in place of the bending actuator to achieve a similar result, as illustrated in FIG. 7D.

Figure 7C:
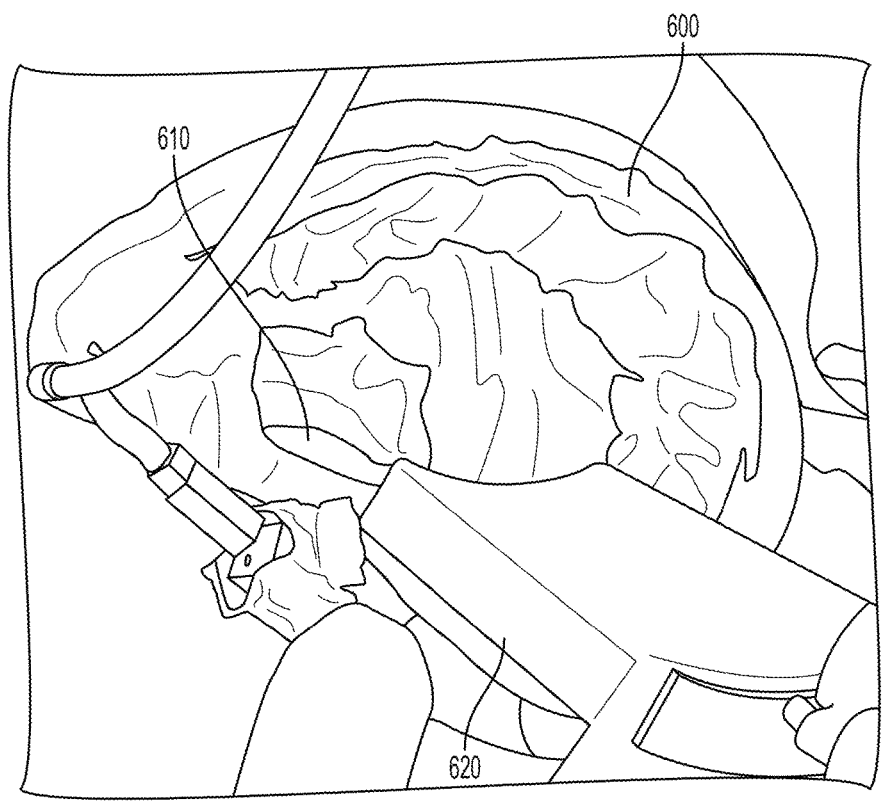
FIG. 7C presents a physical embodiment of a deep pelvic retractor being used in conjunction with the tissue retractor on cadaveric tissue according to one or more embodiments.
Figure 7D:
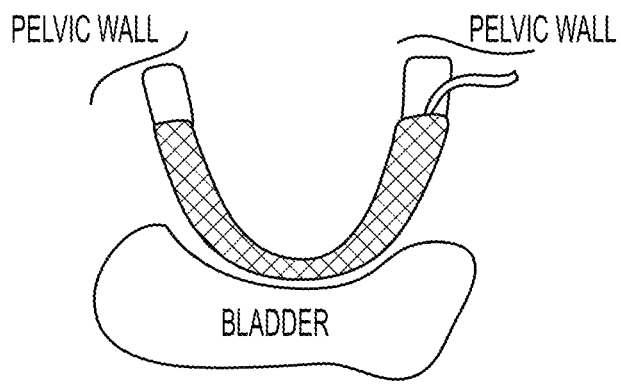
FIG. 7D depicts a soft actuator that anchors to the pelvic wall and bends (or extends) to displace the bladder according to one or more embodiments.

FIG. 7C presents a physical embodiment of the DPR being used in conjunction with the tissue retractor on cadaveric tissue. The tissue retractor 600 holds the incision open, while the deep pelvic retractor 610 is inserted in the body opening. The location and angle of the DPR can be adjusted using handle 620. FIG. 7D depicts another embodiment of a soft retractor that anchors to the pelvic wall (e.g. screwed or pinned in place) and bends (or extends) to displace the bladder. This soft retractor could also be position to apply pressure at critical spots to control internal bleeding.

Figure 8A:
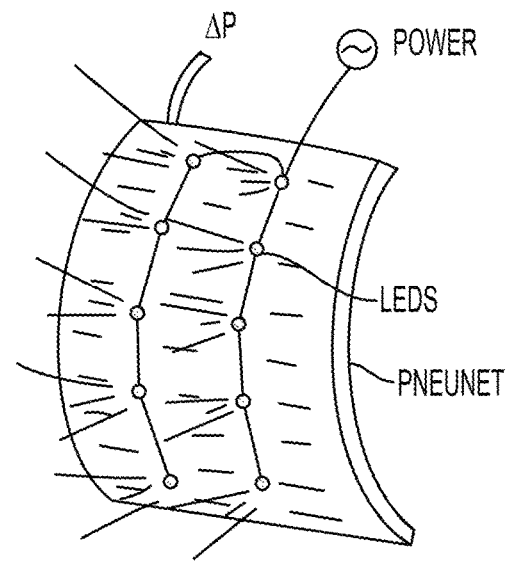
FIGS. 8A and 8B depict the incorporation of electronic circuitry into the device to (A) provide LED lighting to illuminate the deep pelvic retractor and (B) to provide LED lighting to illuminate the soft retractor used at incision sites.

The soft body retractor can be equipped with other functionalities, such as LED lighting, RFID tags, visualizing capability and diagnostics. FIG. 8A depicts a paddle retractor (like the DPR) with electronics and LEDs embedded in the structure. This feature can help improve visibility in difficult to illuminate areas.

Figure 8B:
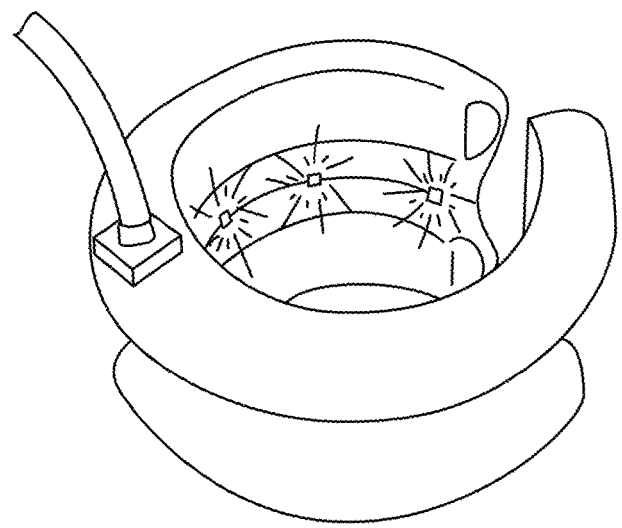

FIG. 8B depicts the self-retaining tissue retractor with electronics and LEDs embedded in the structure. This feature can help improve visibility in difficult to illuminate areas.

Other electronic capabilities can also be integrated into these designs. For example, the tissue retractor could be outfitted with an RFID tag reader which can be used to count medical instruments that enter the body. A visual indicator (e.g. green LED=all instruments are recovered, red LED=not all instruments recovered) could be used to notify medical personnel if all the instruments have been collected and/or a list of instruments that are in the body can be wirelessly sent to a computer and projected on a monitor. The electronics device can include electronics for measuring impedance (e.g., measuring tissue impedance as an indicator of tissue health after cauterization), electronics for electrochemical sensing (e.g., for medical diagnostics). These electronics could also be used as part of a suit of diagnostic sensors for detecting the margins of abnormal tissue or the presence of bacterial to list two examples.

In addition the soft retractor can include other functionalities. For example, the soft retractor can provide lumens for access to the body cavity. The lumens can be equipped with irrigators for irrigating a body cavity, or for delivering therapies, or insertion of surgical equipment, or for providing suction. The soft retractor can be used for intubation. For example, the soft actuator lumens can be equipped with tissue excision (e.g. biopsy), for introduction of stiff materials/objects, for suction to remove fluids from a cavity or for intubation. The lumens can also be designed to accommodate medical diagnostic sensors for detecting cancerous tissue, bacteria, HIV, etc.

In other embodiments, the soft retractor can include features that assist in securing, such as suction cups for grabbing or anchoring to anatomical structures, or surgical nails or screws for similar purposes. Other functional materials can be included, such as absorbent materials, blood clotting agents, antimicrobial, antibiocidal agents and the like.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially, though not perfectly pure, as practical and imperfect realities may apply; e.g., the potential presence of at least trace impurities (e.g., at less than 1 or 2%) can be understood as being within the scope of the description; likewise, if a particular shape is referenced, the shape is intended to include imperfect variations from ideal shapes, e.g., due to manufacturing tolerances. Percentages or concentrations expressed herein can represent either by weight or by volume.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments. Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly. Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise.

It will be appreciated that while a particular sequence of steps has been shown and described for purposes of explanation, the sequence may be varied in certain respects, or the steps may be combined, while still obtaining the desired configuration. Additionally, modifications to the disclosed embodiment and the invention as claimed are possible and within the scope of this disclosed invention. In addition, all embodiments are intended to be used individually or in combination with any one or more of the embodiments disclosed herein.

The invention claimed is:

1. A method of forming a soft material device comprising at least a first and second soft actuators comprising a first and second pressurizable interior spaces, respectively, the method comprising:
   providing a first mold comprising:
     a first soft actuator mold body;
     a second soft actuator mold body; and
     a bridging channel connecting the first and second soft actuator mold bodies;

casting a first material having a first durometer into the first mold to form a molded part comprising a first and second actuators connected by a bridge; wherein the first and second actuators comprises the first and second pressurizable interior spaces, respectively;

transferring the molded part into a second mold comprising a plurality of cavities;

casting a second material having a second durometer higher than the first durometer into the cavities to form a plurality of structural features on at least a portion of the surfaces of the first and second actuators; and removing the formed soft material device from the second mold.

2. The method of claim 1, further comprising inserting a first and second rods into the first and second soft actuator mold bodies, respectively; wherein the first and second rods define the first and second pressurizable interior spaces, respectively.

3. The method of claim 1, further comprising sealing the ends of the first and second elastomeric actuators.

4. The method of claim 1, wherein the first and/or second soft actuator mold bodies comprise a plurality of depressions.

5. The method of claim 1, wherein the first and second materials are each elastomeric material.

6. The method of claim 5, wherein the first and second materials are each made from rubber.

7. The method of claim 1, wherein the first material is an elastomeric material and the second material comprises an inextensible fiber.

8. The method of claim 7, wherein the second material comprises a plurality of composite sheets reinforced by the inextensible fiber.

9. The method of claim 1, wherein the first and second soft actuators each comprise a plurality of pressurizable interior spaces.

10. The method of claim 1, wherein the first and/or second soft actuators are a finger actuator.

11. The method of claim 1, wherein the first and/or second soft actuators are a liner extending actuator.

12. The method of claim 1, further comprising attaching a fluid line to the first and/or second pressurizable interior spaces.

13. The method of claim 12, wherein the fluid line is attached to a pressurizing source.

* * * * *